US011019319B2

(12) United States Patent
Chen

(10) Patent No.: US 11,019,319 B2
(45) Date of Patent: May 25, 2021

(54) SYSTEMS AND METHODS FOR CONTROLLED DICHOPTIC VIEWING

(71) Applicant: Tufts Medical Center, Inc., Boston, MA (US)

(72) Inventor: Vicki M. Chen, Lexington, MA (US)

(73) Assignee: Tufts Medical Center, Inc., Boston, MA (US)

(*) Notice: Subject to any disclaimer, the term of this patent is extended or adjusted under 35 U.S.C. 154(b) by 256 days.

(21) Appl. No.: 16/242,655

(22) Filed: Jan. 8, 2019

(65) Prior Publication Data
US 2019/0209003 A1 Jul. 11, 2019

Related U.S. Application Data

(60) Provisional application No. 62/615,519, filed on Jan. 10, 2018.

(51) Int. Cl.
| *H04N 9/80* | (2006.01) |
| *H04N 9/64* | (2006.01) |
| *G11B 27/00* | (2006.01) |
| *A61B 3/08* | (2006.01) |
| *H04N 5/76* | (2006.01) |
| *A61B 3/02* | (2006.01) |
| *A61B 3/028* | (2006.01) |

(52) U.S. Cl.
CPC .............. *H04N 9/80* (2013.01); *A61B 3/08* (2013.01); *G11B 27/00* (2013.01); *H04N 9/64* (2013.01); *A61B 3/022* (2013.01); *A61B 3/028* (2013.01); *H04N 5/76* (2013.01)

(58) Field of Classification Search
CPC .......... A61B 3/028; A61B 3/022; A61B 3/08; H04N 9/64; H04N 9/80; H04N 5/76; G11N 27/00; A61F 9/022; A61F 9/00829
USPC ...................................................... 382/154
See application file for complete search history.

(56) References Cited

U.S. PATENT DOCUMENTS

| 2012/0179076 A1* | 7/2012 | Bavelier | A61H 5/005 601/37 |
| 2018/0311103 A1* | 11/2018 | Succar | A61H 5/005 |
| 2019/0125180 A1* | 5/2019 | Arnold | A61B 3/10 |

* cited by examiner

*Primary Examiner* — Daniel G Mariam
(74) *Attorney, Agent, or Firm* — Occhiuti & Rohlicek LLP

(57) ABSTRACT

Disclosed are implementations, including a method for video presentation to cause controllable stimulation of a subject's eyes, that includes preparing a video presentation comprising successive frames of moving images, and, for one or more of the successive frames, selecting a target feature(s) represented in the moving images, with the moving images further comprising one or more background features, the target feature causing stimulation of one of a first eye or a second eye of the subject. For at least some of the frames in which the target feature(s) appears, the method also includes controlling a first contrast characteristic of the target feature(s) to form a first portion of the moving images, and controlling a second contrast characteristic of the one or more background features to form a second portion of the moving images. The method further includes providing the prepared video presentation.

37 Claims, 7 Drawing Sheets

250

260 — Obtaining a video presentation comprising successive frames of moving images. At least one or more of the successive frames include a selected at least one target feature represented in the moving images and configured to cause stimulation of one of a first eye or a second eye of the subject, and one or more background features, with the at least one target feature being instrumental in carrying out the message or story of the video presentation and being distinguishable from a remainder of the moving images comprising the one or more background features. For at least some of the one or more of the successive frames in which the at least one target feature appears, a first contrast characteristic of the target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images.

270 — Presenting the prepared video presentation comprising the first portion of the moving images to the first eye of the subject, and the second portion of the moving images to the second eye.

FIG. 2B

SYSTEMS AND METHODS FOR CONTROLLED DICHOPTIC VIEWING

CROSS-REFERENCE TO RELATED APPLICATIONS

This application claims the benefit of U.S. Provisional Application No. 62/615,519, filed Jan. 10, 2018, the contents of which are incorporated by reference.

BACKGROUND

Stereoacuity is defined as the ability to detect small differences in the position of the same object when viewed simultaneously by each eye. In layman's terms, stereoacuity provides the perception of depth or 3-dimensions. Deficiencies in stereoacuity can be caused by any ocular or neurologic condition that causes an object to be perceived unequally between the eyes. Typical causative medical conditions include amblyopia (lazy eye syndrome) and strabismus (ocular misalignment) in which one eye is dominant and may actively suppress information received by the non-dominant eye. This results in unequal perception of visual stimuli. Even when amblyopia and strabismus are fully treated at a young age, available therapies only partially restore stereoacuity in 15-54% of patients. Anti-suppression as an approach to amblyopia treatment was reported in optometric literature as early as the 1970's; video games for amblyopia treatment and orthoptic therapy were proposed in the 1980s. While patching and penalization are currently the standard for amblyopia treatment, these methodologies generally suffer from poor compliance and may potentially compromise binocular visual development.

SUMMARY

In some variations, a method for video presentation to cause controllable stimulation of a subject's eyes is provided. The method includes preparing a video presentation including successive frames of moving images, and, for one or more of the successive frames, selecting at least one target feature represented in the moving images, with the moving images further comprising one or more background features, the at least one target feature causing stimulation of one of a first eye or a second eye of the subject, with the at least one target feature being instrumental in carrying out the message or story of the video presentation and being distinguishable from a remainder of the moving images comprising the one or more background features. For at least some of the one or more of the successive frames in which the at least one target feature appears, the method also includes controlling a first contrast characteristic of the at least one target feature in each frame of the moving images in which the at least one target feature is present to form a first portion of the moving images, and controlling a second contrast characteristic of the one or more background features in the each frame of the moving images in which the one or more background features are present to form a second portion of the moving images. The method further includes providing the prepared video presentation comprising the first portion of the moving images configured to be presented to the first eye of the subject, and the second portion of the moving images configured to be presented to the second eye of the subject.

Embodiments of the method may include at least some of the features described in the present disclosure, including one or more of the following features.

Providing the prepared video presentation may include storing the prepared video presentation on a data storage device configured to be read at a subsequent time instance by a video player device for presentation of the stored video presentation to the subject.

Providing the prepared video presentation may include presenting the first portion of the moving images and the second portion of the moving images to the first eye and the second eye of the subject improves stereoacuity of the subject.

Providing the first portion and the second portion of the moving images may include generating a dichoptic video presentation comprising the first portion of the moving images and the second portion of the moving images, including presenting the first portion of the moving images in first one or more colors that are visible through a first filtering lens configured to inhibit visibility of second one or more colors, and presenting the second portion of the moving images in the second one or more colors that are visible through a second filtering lens configured to inhibit visibility of the first one or more colors.

Presenting the first portion of the moving images in the first one or more colors may include presenting the first portion of the moving images in a red-based color visible through a green-based filtering lens and suppressed by a red-based filtering lens. Presenting the second portion of the moving images in the second one or more colors may include presenting the second portion of the moving images in a green-based color visible through the red-based filtering lens and suppressed by the green-based filtering lens.

Presenting the first portion of the moving images in the first one or more colors may include presenting the first portion of the moving images in a green-based color visible through a red-based filtering lens and suppressed by a green-based filtering lens. Presenting the second portion of the moving images in the second one or more colors may include presenting the second portion of the moving images in a red-based color visible through the green-based filtering lens and suppressed by the red-based filtering lens.

Presenting the second portion of the moving images in the green-based color may include presenting the second portion of the moving images in a green-and-grey color combination visible through the red-based filtering lens and suppressed by the green-based filtering lens.

Providing the prepared video presentation further may include presenting the first portion of the moving images to the first eye affected by an amblyopia condition.

Preparing the video presentation may include generating an animated video presentation comprising an animated target feature and animated one or more background features.

Preparing the video presentation may include receiving source video images, and identifying from the source video images outlines of a first object and one or more second objects, with the first object corresponding to the at least one target feature and the one or more second objects corresponding to the one or more background features.

The method may further include extracting the identified outlines of the first object corresponding to the at least one target feature, extracting the identified outlines of the one or more second objects, and processing the extracted outlines of the first object and the one or more second objects to include optical wavelengths (and/or directions) with characteristics matching a filtering spectrum of anaglyph glasses used by the subject to view the video presentation.

Processing the extracted outlines may include controllably adjusting gain values for the extracted outlines of the first object and the one or more second objects, controllably adjusting luminance of the moving images, and controllably adjusting chromatic components for the first object and the one or more second objects.

Controlling the second contrast characteristic of the one or more background features may include applying the second contrast characteristic to the one or more background features so that, when viewed by the subject, a perceived background feature contrast level of the one or more background features is approximately 10-20% of a perceived target feature contrast level for the at least one target feature.

The second contrast characteristic may have a lower contrast than the first contrast characteristic.

The method may further include determining the first contrast characteristic of the at least one target feature and the second contrast characteristic of the one or more background features based, at least in part, on contrast testing data for the subject, obtained from a subjective evaluation performed for the subject according to a perceptual contrast testing procedure.

The subjective evaluation performed according to the perceptual contrast testing procedure may be performed according to a MARS PERCEPTRIX™ (Mars) exam.

Determining the first contrast characteristic and the second contrast characteristic may include obtaining the contrast testing data representative of a comparison of Mars exam panels, comprising letters with varying contrast levels, to levels of perception for each eye of the subject, when wearing anaglyph glasses, to the at least one target feature and the at least one background feature, and determining the first contrast characteristic and the second contrast characteristic based on the contrast testing data obtained from the subjective evaluation performed according to the perceptual contrast testing procedure.

Determining the first contrast characteristics and the second contrast characteristics may include adjusting the first contrast characteristic and the second contrast characteristic such that a perceived background feature contrast level of the one or more background features, when viewed by a weaker eye covered by one of the lenses of the anaglyph glasses, is reduced for the at least one target feature.

The method may further include modulating the intensity of at least one of the first portion of the moving images and the second portion of the moving images.

The method may further include presenting the video presentation to a subject affected by deficient stereoacuity or amblyopia.

The method may further include presenting the video presentation to achieve stereoacuity improvements in vision characteristics of a subject with normal stereoacuity levels.

Presenting the video presentation to the subject affected by the amblyopia condition may include presenting the video presentation to the subject such that the at least one target feature is more prominently visible through the subject's eye affected by the amblyopia condition, with the at least one target feature being less visible on the subject's other eye relative to a level of visibility of the at least one target feature through the subject's eye affected by the amblyopia condition (non-dominant eye).

In some variations, a system for video presentation to cause controllable stimulation of a subject's eyes is provided. The system includes a video processor configured to prepare a video presentation including successive frames of moving images. For one or more of the successive frames, the video processor is configured to select at least one target feature represented in the moving images, with the moving images further comprising one or more background features, the at least one target feature causing stimulation of one of a first eye or a second eye (or both eyes) of the subject, with the at least one target feature being instrumental in carrying out the message or story of the video presentation and being distinguishable from a remainder of the moving images comprising the one or more background features. For at least some of the one or more of the successive frames in which the at least one target feature appears, the video processor is also configured to control a first contrast characteristic of the at least one target feature in each frame of the moving images in which the at least one target feature is present to form a first portion of the moving images, and control a second contrast characteristic of the one or more background features in the each frame of the moving images in which the one or more background features are present to form a second portion of the moving images. The system additionally includes an output device configured to provide the prepared video presentation comprising the first portion of the moving images configured to be presented to the first eye of the subject, and the second portion of the moving images configured to be presented to the second eye of the subject.

Embodiments of the system may include at least some of the features described in the present disclosure, including at least some of the features described above in relation to the method, as well as one or more of the following features.

The output device may include a storage device to store output video data representative of the prepared video presentation, the output video data configured to be read at a subsequent time instance by a video player device for presentation of the stored video presentation to the subject.

The output device may include a video presentation unit configured to present the first portion of the moving images and the second portion of the moving images to the first eye and the second eye of the subject such that the first portion of the images is presented to the first eye and the second portion of the images is presented to the second eye of the subject.

The system may further include anaglyph glasses wearable by the subject to view the video presentation.

In some variations, a kit is provided that includes a video storage device comprising non-transitory video-recording medium storing video data representative of successive frames of moving images. One or more of the successive frames include a selected at least one target feature represented in the moving images, with the moving images further comprising one or more background features, the at least one target feature causing stimulation of one of a first eye or a second eye (or both eyes) of the subject, with the at least one target feature being instrumental in carrying out the message or story of the video presentation and being distinguishable from a remainder of the moving images comprising the one or more background features. For at least some of the one or more of the successive frames in which the at least one target feature appears, a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images. The kit also includes anaglyph glasses wearable by a subject to view a video presentation generated when the video data representative of the successive frames of the moving images is decoded and played on a video presentation unit.

Embodiments of the kit may include at least some of the features described in the present disclosure, including at least some of the features described above in relation to the method and the system, as well as one or more of the following features.

The kit may further include the video presentation unit.

In some variations, another kit is provided that includes a video access device to access video data representative of successive frames of moving images. One or more of the successive frames include a selected at least one target feature represented in the moving images, with the moving images further comprising one or more background features, the at least one target feature causing stimulation of one of a first eye or a second eye (or both eyes) of the subject, with the at least one target feature being instrumental in carrying out the message or story of the video presentation and being distinguishable from a remainder of the moving images comprising the one or more background features. For at least some of the one or more of the successive frames in which the at least one target feature appears, a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images. The kit also includes anaglyph glasses wearable by a subject to view a video presentation generated when the video data representative of the successive frames of the moving images is decoded and played on a video presentation unit.

Embodiments of the other kit may include at least some of the features described in the present disclosure, including at least some of the features described above in relation to the method, the system, and the first kit, as well as one or more of the following features.

The video access device may be configured to access one or more of, for example, a video storage device comprising non-transitory video-recording medium storing the video data, and/or a remote device configured to stream the video data to a device accessible by the subject.

In some variations, another method for video presentation to cause controllable stimulation of a subject's eyes is provided. The method includes obtaining a video presentation comprising successive frames of moving images, with one or more of the successive frames including a selected at least one target feature represented in the moving images and configured to cause stimulation of one of a first eye or a second eye (or both eyes) of the subject, and one or more background features, with the at least one target feature being instrumental in carrying out the message or story of the video presentation and being distinguishable from a remainder of the moving images comprising the one or more background features. For at least some of the one or more of the successive frames in which the at least one target feature appears, a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images. The method further includes presenting the prepared video presentation comprising the first portion of the moving images to the first eye of the subject, and the second portion of the moving images.

Embodiments of the additional method may include at least some of the features described in the present disclosure, including at least some of the features described above in relation to the first method, the system, and the kits, as well as one or more of the following features.

Obtaining the video presentation may include one or more of, for example, receiving a video transmission from a remote device via a communication channel connecting the remote device to a video presentation unit, and/or reading video presentation data for the video presentation from a data storage device.

Presenting the prepared video presentation may include presenting the prepared video presentation to a subject to improve stereoacuity of the subject.

The video presentation is processed at a video processor from received source video images, with the video processor configured to identify from the source video images outlines of a first object and one or more second objects, with the first object corresponding to the at least one target feature and the one or more second objects corresponding to the one or more background features.

The video processor may further be configured to extract the identified outlines of the first object corresponding to the at least one target feature, extract the identified outlines of the one or more second objects, and process the extracted outlines of the first object and the one or more second objects to include optical wavelength characteristics matching a filtering spectrum of anaglyph glasses used by the subject to view the video presentation.

Presenting the prepared video presentation may include presenting the prepared video presentation to the subject wearing anaglyph glasses to view the video presentation.

In some variations, a video storage device is provided that includes non-transitory video-recording medium storing video data representative of successive frames of moving images. One or more of the successive frames include a selected at least one target feature represented in the moving images, with the moving images further comprising one or more background features, the target feature causing stimulation of one of a first eye or a second eye (or both eyes) of the subject, with the target feature being instrumental in carrying out the message or story of the video presentation and being distinguishable from a remainder of the moving images comprising the one or more background features. For at least some of the one or more of the successive frames in which the at least one target feature appears, a first contrast characteristic of the target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images.

Embodiments of the video storage device may include at least some of the features described in the present disclosure, including at least some of the features described above in relation to the methods, the system, and the kits.

Other features and advantages of the invention are apparent from the following description, and from the claims.

BRIEF DESCRIPTION OF THE DRAWINGS

These and other aspects will now be described in detail with reference to the following drawings.

FIG. 2B is a flowchart of an example procedure, generally performed at a video presentation station/unit, for video presentation to cause controllable stimulation of a subject's eyes is shown.

Like reference symbols in the various drawings indicate like elements.

DESCRIPTION

Figure 1:
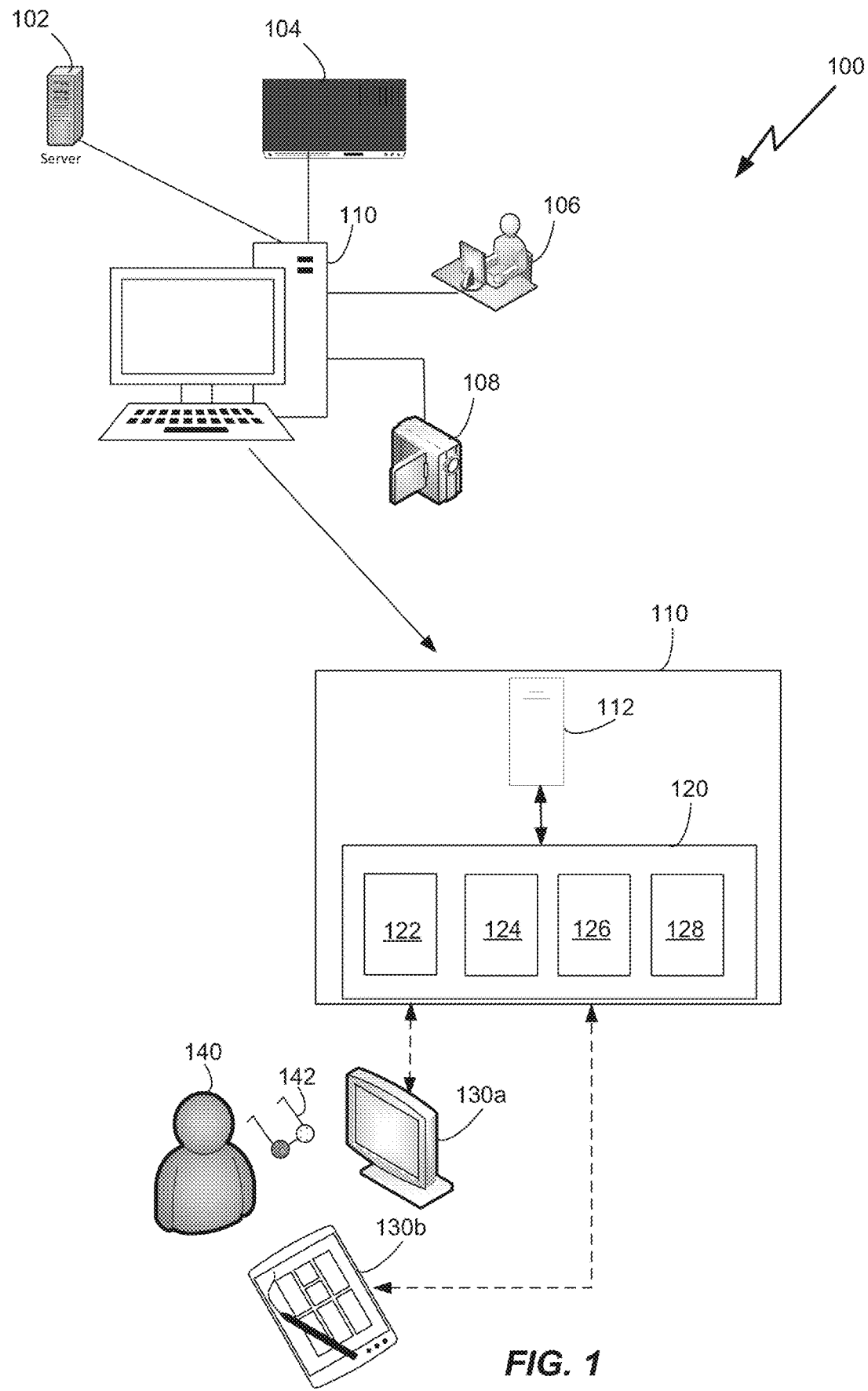
FIG. 1 is a diagram of an example video presentation system to cause controllable (unequal or variable) stimulation of a subject's eyes.

Disclosed herein are methods, systems, devices, media, and other implementations to improve persons' stereoacuity and vision. Under the approaches described herein, videos are generated containing images that are viewed differently by each eye (e.g., viewed differently by the non-dominant, or weaker eye, in the case of a person with amblyopia condition, than by that person's other, stronger, eye). A person viewing the video through, for example, special glasses is forced to combine the images in the person's brain in order to make sense of the story presented via the video. In some embodiments, the videos generated are red-green-based videos (e.g., the visual objects in the videos are implemented with specific combinations of red, green and blue pigments in order to achieve a particular red, green, or grey color hue). The glasses and video used in concert are generally easier and less costly (in terms of preparation time, machinery/apparatus used, etc.) than some other approaches (e.g., 3D movie viewed on 3D monitors) that are used to improve stereoacuity and/or to treat various conditions manifested as degraded stereoacuity levels. In some embodiments, videos may be generated to include other color spectrums (e.g., yellow-blue, or some other color combinations). The videos generated according to the approaches described herein can be viewed at home, on a subject's own equipment (laptop computer, iPad, etc.), and require generally inexpensive viewing accessories (e.g., red-green anaglyph glasses), making the approaches described herein accessible to most subjects.

Thus, in some embodiments, a system for video presentation to cause controllable stimulation of a subject's eyes (e.g., provide variable or unequal visual stimulation to the different eyes of the subject) is provided. The system includes a video processor configured to prepare a video presentation (e.g., processing existing videos, or generating new videos using, for example, computer animation applications, or original video recordings) that include successive frames of moving images. For one or more of the successive frames, the video processor is configured to select or identify at least one target feature represented in the moving images (alternatively, a target feature(s) can initially be identified by a person, and thereafter the video processor can identify/track that target feature in subsequent frames), with the moving images further including one or more background features, to cause stimulation of one of a first eye or a second eye (or both eyes) of the subject. The at least one target feature is a feature/object that is instrumental in carrying out the message or story of the video presentation (i.e., the central character in the video presentation) and is distinguishable from a remainder of the moving images comprising the one or more background features. Selection of the at least one target feature is directed by the prescribing physician. For at least some of the one or more of the successive frames in which the at least one target feature appears, the video processor is configured to control a first contrast characteristic of the at least one target feature in each frame of the moving images in which the at least one target feature is present to form a first portion of the moving images, and control a second contrast characteristic of the one or more background features in the each frame of the moving images in which the background figure is present to form a second portion of the moving images. The example system described herein further includes a video presentation unit (e.g., a unit of preferably at least 9 inches in diagonal measurement, which may include such devices as a tablet device, a laptop computer, a video projector, a dedicated LCD or plasma screen, etc.; other video presentation unit sizes and dimensions may also be used) configured to present the first portion of the moving images and the second portion of the moving images to the first eye and the second eye of the subject such that the first portion of the images is presented to the first eye and the second portion of the images is presented to the second eye of the subject. The selective presentation of the video portions (which include the at least one target feature(s) and the background features) may be achieved using anaglyph glasses worn by the subject through which the video presentation is to be viewed. Videos presented may include 20-minutes videos (or some other duration), with a recommended total daily viewing time being 40 minutes a day. In some embodiments, the video presentation may correspond to gaming content comprising features processed or generated (for color, contrast, and/or other attributes) in the manner described herein.

Also described herein are implementations that include a method for video presentation to cause controllable stimulation of a subject's eyes, with the method including preparing a video presentation including successive frames of moving images. For one or more of the successive frames, the method includes, selecting (e.g., based on input from a user, based on metadata included with a source video, based on analysis performed using a learning engine, etc.) at least one target feature represented in the moving images, with the moving images further comprising one or more background features, the at least one target feature causing stimulation of one of a first eye or a second eye (or, in some embodiments, both eyes) of the subject, with the at least one target feature being instrumental in carrying out the message or story of the video presentation and being distinguishable from a remainder of the moving images comprising the one or more background features. For at least some of the one or more of the successive frames in which the at least one target feature appears, the method includes controlling a first contrast characteristic of the at least one target feature (e.g., maintaining or modifying a relative contrast level of the at least one target feature relative to the contrast levels of other features in the frames of the video presentation) in each frame of the moving images in which the at least one target feature is present to form a first portion of the moving images, and controlling a second contrast characteristic of the one or more background features in the each frame of the moving images in which the one or more background features are present to form a second portion of the moving images. The method additionally includes providing the first portion of the moving images and the second portion of the moving images (the first and second portions containing features of differing contrasts and/or differing other attributes controlling the perceptibility of the features) to each of the eyes of the subject such that the first portion of the images is presented to one eye and the second portion of the images is presented to another eye of the subject.

Thus, with reference to FIG. 1, a schematic diagram of an example video presentation system 100 to cause controllable stimulation of a subject's eyes is shown. The video presentation system includes a video processor 110 that is configured to process video data, including to render graphical content (such as generated animation), to process input video data (such as previously generated video content), and/or to perform the procedures and operations described herein. The video presentation may be prepared based on source materials from an existing video, e.g., provided as coded video data from a remote network server 102 via a wired or wireless communication link, established using a wired network interface such as a USB connection (not shown in FIG. 1), or via a wireless interface implemented using a WLAN or WWAN transceiver (not shown in FIG. 1). Source material from an existing video may also be provided using a non-transitory media such as a DVD or Blu-Ray™ disc played on a DVD/Blu-Ray™ player 104 coupled to the video processor 110. Alternatively, or additionally, original source materials may be prepared by a user 106 (e.g., an artist, such as an animator). In some embodiments, the source input video may be a recording captured via a video camera such as a camera 108. The video content output generated by the video processor 110 is presented on a video presentation unit such as a monitor/display 130a (in wired or wireless communication with the video processor 110), a tablet device 130b (e.g., wireless tablet device) where it viewed by a subject 140 equipped with viewing apparatus such as anaglyph or polarized 3D glasses (e.g., red-green glasses) 142. Where the video is transmitted to the video presentation unit from a remote video processor 110 (through a wired or wireless network communication channel), the video processor (or the communication module connected thereto) may be configured to stream the generated video data to the video presentation unit. In some embodiments, the subject may be provided with an access card (containing a written code or an electronic circuit, such as a SIM card, to facilitate access) to authorize/allow a personal device used by the user/subject to access the remote video processor (or some other remote data repository) and download (e.g., have the video processor stream) content corresponding to the video data generated by the video processor. The anaglyph glasses include different color filtering lenses that each covers one of the subject's eyes, with each lens configured to suppress features in the video presentation matching the filtering spectrum of the corresponding lens. By preparing or generating video content that includes features with controllably adjusted attributes (color content, intensity, luminance), stereoacuity of the subject can be improved by presenting certain features to one eye (e.g., a non-dominant or weaker eye of a person with amblyopia), and other features to the other eye.

The video processor 110 may comprise one or more processor-based devices 112, such as a general programmable processor (or microprocessor), a microcontroller, special purpose logic circuitry (e.g., an FPGA (field programmable gate array), an ASIC (application-specific integrated circuit), etc.) that provide processing functions, a dedicated video processor such a graphics processing unit (GPU), an accelerated processing unit (APU), as well as other types of processing modules. The video processor 110 may include one or more memory devices 120 for storing data, e.g., the input video data, and resultant output video data generated from the input video data, and software instructions for executing programmed functionality of the video processor 110 the device. The one or more processor-based devices 112 are coupled to the one or more memory devices. The memory devices may include main memory, cache memory and bus interface circuits (not shown), as well as mass storage devices such as a hard drive (realize as magnetic discs, solid state (semiconductor) memory devices), flash drive associated with the computer system, etc. In some embodiments, at least some of the video processing functionality described herein may be implemented through dedicated hardware circuitry rather than through programmable software implementations.

More particularly, as depicted in FIG. 1, several modules may be included to implement, e.g., as software realizations (comprising programmable instructions executable on the one or more processing devices included with the video processor 110) the procedures and processes described herein. As noted, at least some of the modules may be realized as dedicated hardware circuit implementations or as combined hardware-software implementations. The modules comprising the video processor 110 include an input stage module 122 configured to receive video input data (e.g., source video) and perform any necessary pre-processing on the video content. For example, the input stage module 122 may be configured to decode the received input data (which may be provided in one of various formats, such as MPEG) and to transform it to a data on which the various processes/procedures described herein may be performed. Additionally, or alternatively, the input stage module 122 may also allow user to generate, or render, original content (e.g., through a commercial or a customized proprietary video editor, through a commercial or proprietary animation application, through an image-capture device such as the video camera 108, etc.), and provide the generated contend in a format on which the processes and procedures described herein can be performed.

As further shown in FIG. 1, the video processor 110 may also include a feature selector 124 (in this example, the feature selector 124 is configured as a software-based module whose executable code is stored in the memory 120 coupled to the one or more processors 112 of the video processor 110) configured to select at least one target feature, represented in the moving images, with the moving images further comprising one or more background features. The at least one target feature is the feature(s) determined to cause stimulation of one of a subject' eye (e.g., the weaker (non-dominant) of the two eyes, where the weakness may be a manifestation of an amblyopia condition). The target feature (also referred to as a salient feature) is instrumental in carrying out the message or story of the video presentation and is distinguishable from a remainder of features in the moving images. In some embodiments, the feature selector 124 may be configured to identify and select the at least one target feature based on such information as user input (e.g., selecting, using a touchscreen, a mouse, or some other input device) an object appearing on a screen. Alternatively, or additionally, selection or identification of a target feature(s) (a central or salient figure in the video presentation) may be determined based on metadata associated with the video data being processed. For example, source video (e.g., a commercial presentation, such as an animated program) may include data identifying characters or objects appearing in individual frames comprising the input video content. The feature selector 124 may be configured to track and/or associate the various objects appearing in the input source video (e.g., based on their shapes, morphologies, and/or other features or attributes, as may be derived using various image processing procedures such as edge detection procedures) with the metadata provided with the source input video. For example, in a video presentation, any character appearing in the frame(s) may be identified and tracked. By tracking occurrences of objects appearing in the various frames, the identity of the objects, as provided through the metadata, can be matched to the various characters. In some embodiments, the metadata may also include coordinates, or other location information, for characters appearing in the video frames.

In situations where no information is available about the narrative content of the video frame (e.g., when there is no metadata to identify characters and/or their respective locations in a video frame), selection/identification of a central object (character) may be derived based on the prominence of the objects within a sequence of frames (e.g., within a 1-minute, 5-minute, or any other duration of a sequence of video frames). For example, objects within video frames can be tracked (based on their shapes/morphological features, or based on other features), and the object that is most prominently displayed (based on its occurrence within the sequence, or relative size compared to other objects) may be deemed to be the central character (and thus to be the target feature that is to be processed in the manner described herein). In some embodiments, a learning engine may be implemented to identify a central character from objects in the video frame. Examples of learning engines may be neural networks (such as convolution neural networks, or CNN's, deep neural networks, or some other neural network configuration). A neural network included multiple processing units, referred to as neurons, which are connected to each other (according to some predetermined configuration) with various weights. The weight values between connections can be varied, to allow the neural network to adapt (or learn) in response to training data it receives. Such training data may include, for example, various video sequences that each include one or more central characters (the target feature(s)) and one or more background features. Other types of learning engines (also referred to as classifiers) include Support Vector Machine (SVM) classifiers, K-Nearest Neighbors (KNN) classifiers, decision tree learning engines, etc.

As further shown in FIG. 1, the video processor may also include a feature attribute controller 126 to controllably process video data associates with the various features or objects identified (e.g., by the feature selector 124) in video frames. The feature attribute controller 126 may be configured to control such feature attributes as a contrast (i.e., the difference in luminance or color between image objects identified in the frames). The feature attribute controller 126 may be configured, in some implementations, to adjust the luminance and/or color characteristics of the at least one target feature (i.e., the central feature or object in the corresponding narrative of the video sequence) so that the resultant output video includes a first portion that is viewable by one eye (e.g., the non-dominant or weaker eye) of the subject, while a resultant second portion (comprising, for example, the background objects or features) is viewable by a second eye (e.g., the dominant or stronger eye) of the subject. For example, the feature attributer controller 126 may be configured to controllably adjust the color characteristics of the at least one target feature to first one or more colors (e.g., a red-based color), while controllably setting the one or more background features to second one or more colors (e.g., green-based color). As will be discussed in greater detail below, the at least one target feature set to the first one or more colors (e.g., red-based colors) can then be viewable through color filtering lenses adapted to suppress the second one or more colors to which the background features have been set (thus reducing the visibility of those features seen through the non-dominant weaker eye). The dominant or stronger eye, on the other hand, will view, through a second color filtering lens configured to suppress the first one or more colors, the background features (which correspond to objects which may be less important or stimulating, from an entertainment or story-telling perspective, than the at least one target feature). As a result, the non-dominant or weaker eye is presented with video portions corresponding to more important or entertaining information, while the stronger eye views the less important or entertaining portions.

Additionally, the feature attributes for the at least one target feature and the one or more background features may be configured to also control the relative contrast of the at least one target feature and the background features so that the background features are at a lower contrast level relative to the at least one target feature (e.g., some percentage value of the contrast level for the target feature, such as 10-20%). The contrast levels for the various features in the video frames may be controlled according to different possible definitions of image/visual contrast (e.g., Weber contrast. Michelson contrast, root-mean-square contrast, etc.) In some embodiments, controlling the contrast level of the various identified features may include maintaining the luminance levels of the at least one target feature (and/or other attributes of the at least one target feature) at their current levels, and adjusting the corresponding levels of the attributes of the background features to values that are some pre-determined relative percentage (e.g., 20% or less), or some ratio of the attribute levels of the at least one target feature. In some variations, the attribute levels for both the at least one target feature(s) and the background features may be controllably adjusted (e.g., in situations where the at least one target feature's luminance is below some threshold value that would make the background features and target feature too faint if the at least one target feature's luminance, and/or other attributes controlling perceived visual contrast, were kept at their current levels).

In some implementations, the processing performed on the video content (e.g., once converted to a pre-determined format, using the input stage module 122, on which the feature selector 124 and feature attribute controller 126 can be applied) can include extracting feature outlines for the various objects in the video frames (e.g., using edge detection processes that may be one of the processes the feature selector 124 is configured to perform), identifying from the extracted outline the target feature(s) and the background features, and controllably adjusting attributes of the extracted features outlines to adjust the colors and contrast levels of the identified features/objects to generate video output configured to improve stereoacuity of the subject's eyes. The processing performed on the input video content provides a first portion of image data containing prominently visible target features (whose chromatic and luminance components have been adjusted to appear, for example, in red-based colors, and whose contrast level relative to the background feature is controllably adjusted to be high) viewable through specialized glasses with appropriate color filtering lens configured to suppress the processed background features. The processing performed on the input video also provides a second portion of the image data that includes the less prominent background features that are viewable through another coloring filtering lens (usually covering the stronger eye) configured to suppress the target feature(s). For example, the background features are controllably adjusted to include chromatic attributes in green-based colors (e.g., green-and-grey color components) that are viewable/noticeable through, for example, a red filtering lens configured to suppress the target feature(s) that was adjusted to include red-based color components.

Thus, in some embodiments, video processor 110 is configured to extract/derive outlines (e.g., using edge detection processing implemented through, for example, the feature selector 124) of a first object corresponding to a target feature (which may be one of the central characters in the narrative of a video presentation), and extract/derive the identified outlines of one or more second objects (the background features, corresponding to less important characters or objects in the narrative of the video). Having extracted the outlines (or otherwise identified and tracked objects in the video frames), the video processor (e.g., via the feature attribute controller 126) is configured to process the extracted outlines of the first object and the one or more second objects to include optical wavelength characteristics matching a filtering spectrum of anaglyph glasses used by the subject to view the video presentation. In some implementations, the feature attribute controller 126 configured to process the extracted outlines may be configured to adjust color and contrast attributes of the extracted features, and thus may be configured to controllably adjust gain values for the extracted outlines of the first object and the one or more second objects, controllably adjust luminance of the moving images, and controllably adjust chromatic components for the first object and the one or more second objects. In some embodiments, the controllable adjustment of attributes of the objects identified in the video frames may also include controllably adjusting the attributes of areas inside the outlines of the features based on the adjusted values of the outlines, e.g., using the same values as the attributes values applied to the outlines, or different values that are a function of the attribute values of the outlines. For example, the area inside the outline may be set to have color compositions that are either suppressed (e.g., the color of the area inside the target feature(s) may be set to a green-based color(s) matching the optical spectrum of the green lens), or are visible, at least partly (e.g., set to color components, such as a grey color combination, that may be viewable via both the red or green lenses of the anaglyph glasses).

In some implementations, the video processor 110 (e.g., via the feature attribute controller 126) may be configured to modulate the attributes of the extracted features to maintain the viewability of the features above a flicker fusion threshold (the threshold where the features are perceived without flickering). For example, the video processor may be configured to modulate the intensity of at least one of a first portion of the moving images (e.g., containing the target feature(s) whose attribute values have been controllably adjusted) and/or the second portion of the moving images (containing the one or more background features). The intensity modulation (e.g., to darken or brighten pixel values corresponding to the features) may be performed on the first and second portion simultaneously, e.g., both the first portion and the second portion may be modulated in similar manner so that the first and second portions are darkened or brightened at the same time, although possibly at different intensity variance rates. Alternatively, the intensity modulation of the first and second portions may be performed out-of-step, with the first portion and the second portion periodically varying their intensity at different time instances (i.e., different time-based functions applied to the respective intensity modulation). The intensity modulation applied to the features may be based on such factors as the colors (and thus their optical wavelengths) selected to be applied to the various features to be presented to the subject, physical and physiological characteristics of the subject (age, time of the day at which the viewing of the output video is occurring, etc.), characteristics of the display device on which the video presentation is taking place, etc. In some embodiments, the video processor 110 may be configured to controllably adjust the attributes of the extracted features so that the intensity modulation of the features is below the flicker fusion threshold as a way of grabbing the viewer's (subject's) attention. For example, the attributes controlling the flicker effect experienced by the subject's eyes may be adjusted such that the flicker effect is more pronounced for the non-dominant (weaker) eye, thus causing the subject to pay more attention to the video content presented/provided to the non-dominant eye.

With continued reference to FIG. 1, as noted, the video presentation system 100 includes the video presentation unit 130*a* or 130*b* on which output video (the resultant video content generated based on the processing performed by, for example, the feature selector 124 and the feature attribute controller 126) is presented. The generated output video content may be, in some embodiments, further processed (via an output stage module 128) to convert the output to a desired format and/or compression standard (e.g., an MPEG format, or some other video coding format) required for presentation of the video content on the video presentation unit 130. The output stage module 128 may also perform other type of filtering or processing on the content generated by the feature selector 124 and the feature attribute controller 126 (e.g., noise removal, etc.) As noted, the video presentation unit may be a monitor or a display such as a display of a handheld tablet device (e.g., a wireless tablet device such as the device 130*b* of FIG. 1), an LCD (liquid crystal display) monitor (such as the device 130*a* of FIG. 1), or some other display, which may located in proximity to the video processor 110 (and be directly physically coupled thereto), or may be located remotely from the video processor and receive output from the video processor via a network connection (wired or wireless). Although not shown in FIG. 1, in some embodiments, the video presentation unit may not be coupled to the video processor 110, but instead may receive the output video generated by the video processor via, for example, portable storage device (discs, flash memory devices, etc.) that store data representative of the output video generated by the video processor 110, or through a wireless transmission (downloadable via a wireless network node). In such embodiment, the video presentation unit may include, or may be coupled to, a media player to access and read the data stored on such storage device, and convert the data (if necessary) to a data format that can be processed and displayed on the media player. Additionally, in such embodiments, the video processor may be coupled to an output device such a data storage/writing device to write the video processor's output data to, for example, a portable storage device. The video presentation unit 130 may include a touchscreen to allow the subject viewing the video presentation to provide user input to allow interaction between the subject and the video presentation system 100. The subject 140 may provide input to cause necessary adjustments to the processing performed by the video processor 110. For example, the subject 140 can provide input indicating the level of ease at which it can view the video presentation, to indicate any displeasing artifact or difficulties in viewing the presentation (e.g., indicate if there is a flickering of the features presented via the video presentation unit), and so on. The video presentation unit 130 is thus configured to present the first portion of the moving images and the second portion of the moving images to the first eye and the second eye of the subject such that the first portion of the images is presented to the first eye and the second portion of the images is presented to the second eye of the subject. The video presentation unit 130 configured to present the video presentation to the subject affected by amblyopia or deficient stereoacuity is configured to present the video presentation to the subject such that the at least one target feature is more prominently visible through the subject's eye affected by amblyopia or non-dominant eye, with the at least one target feature being less visible on the subject's other eye relative to a level of visibility of the at least one target feature through the subject's weaker eye affected by amblyopia. In subjects fully treated for amblyopia, one eye is typically dominant while the other is suppressed under viewing conditions that require fusion of central vision. In such cases, the main target feature is more prominently visible through the subject's non-dominant eye and is less prominently visible through the dominant eye.

Figure 2A:
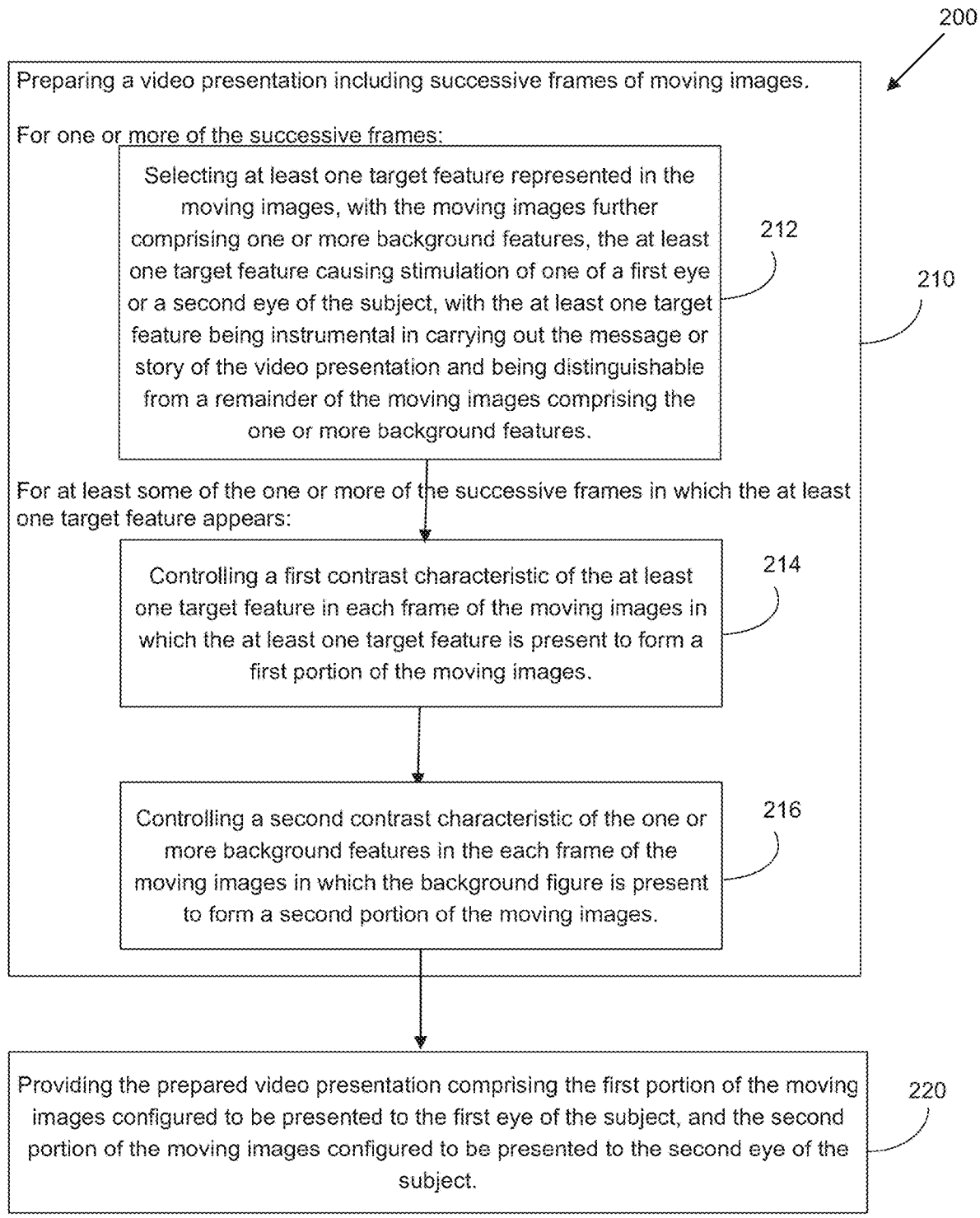
FIG. 2A is a flowchart of an example procedure, generally performed at a video processing system, for video to cause controllable stimulation of a subject's eyes.

With reference next to FIG. 2A, a flowchart of an example procedure 200, generally performed at a video processing system (such as at least parts of the system 100 of FIG. 1) for video presentation to cause controllable stimulation of a subject's eyes (e.g., by causing unequal/non-uniform visual stimulation of the eyes) is shown. As discussed herein, the procedure 200 can be used to improve stereoacuity and vision of a subject, e.g., to improve a person's ability to process visual information from both eyes, to mitigate vision problems caused by certain vision conditions (such as amblyopia), and so on. The procedure 200 includes preparing 210 a video presentation (e.g., using a video processor such as the video processor 110 of the system 100 depicted in FIG. 1) including successive frames of moving images. As noted, the video presentation may be prepared based on source materials from an existing video (e.g., provided as coded video data from the remote network server 102 of FIG. 1, or provided from a non-transitory media such as a DVD or Blu-Ray™ disc played on the media player 104 coupled to the video processor 110). Or may be generated based on newly created original video material.

As illustrated in box 210, for one or more of the successive frames, preparing the video presentation includes selecting 212 at least one target feature represented in the moving images, with the moving images further comprising one or more background features, the at least one target feature (the central character) causing stimulation of one of a first eye or a second eye of the subject, with the at least one target feature being instrumental in carrying out the message or story of the video presentation and being distinguishable from a remainder of the moving images comprising the one or more background features.

Additionally, for at least some of the one or more of the successive frames in which the at least one target feature appears, the processes of the procedure 200 include controlling 214 a first contrast characteristic of the at least one target feature in each frame of the moving images in which the at least one target feature is present to form a first portion of the moving images, and controlling 216 a second contrast characteristic of the one or more background features in the each frame of the moving images in which the one or more background features are present to form a second portion of the moving images.

In some embodiments, preparing the video presentation may include generating an animated video presentation comprising an animated target feature and animated one or more background features. Thus, in such embodiments, a person (graphic designer or animator) may prepare original source material using, for example, an animation or graphics application (customized application, or commercial application). The person preparing the original content may also identify or designate the target feature(s) and background features to be included in the output video content (i.e., it may not be necessary, in such circumstances, for the feature selector 124 of the video processor to determine automatically which of the features/objects appearing in the input data correspond to the target or background features).

In some implementations, the source materials may be an existing video recording that is to be processed to produce dichoptic video content. In such implementations, preparing the video presentation may include receiving source video images (existing recording delivered from a remote network location or from a media player used to access and play video content stored on non-transitory media, a newly captured video recording obtained with a video camera, etc.), and identifying from the source video images outlines of a first object and one or more second objects, with the first object corresponding to the at least one target feature and the one or more second objects corresponding to the one or more background features. As discussed herein, the derivation of feature outlines may be performed using the feature selector 124 of the video processor 110 of FIG. 1, which may be configured to identify and track features appearing in an image (e.g., through edge detection processing), and/or to determine whether identified features (or outlines thereof) correspond to central characters/objects (target features), or secondary characters/targets. Determination of whether an object is central or secondary may be based on metadata associated with objects in a processed video frame or an image, the output of a learning engine that can analyze the content of a frame or image, or some other processing (e.g., to track the occurrence and prominence of objects in a frame or image). As an example, if the source video is the well-known children's cartoon "Clifford the Big Red Dog" (Scholastic, Inc, NY, N.Y.). Clifford would be the target feature.

As described herein, having identified features/objects appearing in a frame or an image (and/or the narrative role they play in the video sequence), processing, performed using, for example, the feature attribute controller 126 of the video processor 110, is applied to those features to generate the output video content for dichoptic viewing. For example, in some implementations, the processing performed on identified outlines may include extracting the identified outlines of the first object corresponding to the target feature, extracting the identified outlines of the one or more second objects, and processing the extracted outlines of the first object and the one or more second objects to include optical wavelength characteristics matching a filtering spectrum of anaglyph glasses used by the subject to view the video presentation. Thus, the output video generated includes processed extracted features (or their outlines), with at least some of the remainder of the content of the input video frames having been removed (e.g., by desaturating the remainder of the input video to some predetermined color, such as grey). Processing the extracted outlines (or other extracted representations of the objects/ features identified in the moving frames) may include controllably adjusting gain values for the extracted outlines of the first object and the one or more second objects, controllably adjusting luminance of the moving images, and controllably adjusting chromatic components for the first object and the one or more second objects. It is to be noted that in some embodiments, the input source may already be formatted so as to include different layers respectively comprising content corresponding to the target feature(s), the background feature(s), and the remainder of the video (e.g., a de-saturated layer). In such embodiments, the various features may have been extracted, and thus the processing (performed, for example, by the video processor 110) may include setting the color attributes of the various features (in the different layers) to appropriate levels (which may be based on the particular color spectrum of the anaglyph glasses used, on user preferences, etc.)

The processing of features includes controllably adjusting the visual prominence of the target feature(s) and the background feature(s) (e.g., so that a subject can more easily focus its attention and the more visually prominent features that are provided to the subject's non-dominant eye). As noted, one way to control the visual prominence of features is by controlling the relative contrast of the features. For example, in some embodiments, controlling the second contrast characteristic to the one or more background features may include applying the second contrast characteristic to the one or more background features so that, when viewed by the subject, a perceived background feature contrast level of the one or more background features is approximately 10-20% of a perceived target feature contrast level for the target feature. Generally, the controlling of the contrast characteristics of the target and background features causes the second contrast characteristic to have a lower contrast than the first contrast characteristic.

With continued reference to FIG. 2A, the procedure 200 further includes providing 220 the prepared video presentation, comprising the first portion of the moving images configured to be presented to the first eye of the subject, and the second portion of the moving images configured to be presented to the second eye of the subject. The first and second portion may be presented on a video presentation unit (such as the unit 130 of FIG. 1) and viewed by a subject wearing anaglyph glasses (such as the glasses 142 of FIG. 1). In some embodiments, providing the prepared video presentation may include storing the prepared video presentation on a data storage device configured to be read at a subsequent time instance by a video player device for presentation of the stored video presentation to the subject. Thus, once generated, the video presentation may be stored on a storage device (e.g., semiconductor-based storage device, magnetic or optical-based media, etc.) to be subsequently accessed or read for presentation to a subject. The storage device may be a mass storage device located locally where the video processor 110 is located. In such embodiments, the data representative of the video presentation may be communicated (via a wired or wireless link) to a video presentation unit for presentation to the subject. Where a portable storage device (e.g., a flash drive, a DVD disc, etc.) is used, the portable storage device may be received by a media presentation player for playback to present the video presentation to the subject. In some embodiments, the video presentation may be presented directly from the video processor (e.g., substantially in real-time, via a wired or wireless link) to the video presentation unit 130.

As noted, providing the first portion of the moving images and the second portion of the moving images to the first eye and the second eye of the subject improves stereoacuity of the subject. For example, the first portion of the moving images (containing the target feature(s) whose attributes were controllably adjusted to make them more prominent, e.g., in terms of visual contrast levels, than the background features), may be presented to the first eye affected by amblyopia (e.g., by controlling the color components of the target feature(s) to be in colors not suppressed by a color filtering lens covering the first eye affected by amblyopia). In some embodiments, providing the first portion and the second portion of the moving images may include generating a dichoptic video presentation (e.g., using the feature selector 124 and the feature attribute controller 126 of FIG. 1) comprising the first portion of the moving images and the second portion of the moving images. This may include presenting the first portion of the moving images in first one or more colors that are visible through a first filtering lens configured to inhibit visibility of second one or more colors (e.g., because the second one or more colors may be similar to the color of the first filtering lens, consequently causing those color to become less noticeable when passes through that lens), and presenting the second portion of the moving images in the second one or more colors that are visible through a second filtering lens configured to inhibit visibility of the first one or more colors.

In one example, presenting the first portion of the moving images in the first one or more colors may include presenting the first portion of the moving images in a red-based color visible through a green-based filtering lens (of green-red glasses, such as the glasses 142 worn by the subject 140 of FIG. 1) and suppressed by a red-based filtering lens. In some situations, at least a part of the optical content of the first portion, e.g., some grey optical content present in the red-based first portion (as discussed in greater detail below), may pass through the red-based filtering lens and be perceived by the eye covered by that lens. In the present example, presenting the second portion of the moving images in the second one or more colors may include presenting the second portion of the moving images in a green-based color visible through the red-based filtering lens and suppressed by the green-based filtering lens. Presenting the second portion of the moving images in the green-based color may include presenting the second portion of the moving images in a green-and-grey color combination visible through the red-based filtering lens and suppressed by a green-based filtering lens. In some situations, at least a part of the optical content of the second portion, e.g., some of the grey optical content present in the second portion, may pass through the green-based filtering lens and be perceived by the eye covered by that lens. It is to be noted that it may be desirable to not fully suppress grey components because white color can improve contrast (in the case of a non-amblyopic eye, or an otherwise dominant eye, it may be desirable to more substantially suppress grey or white component so as to decrease visibility of certain features, such as the target feature(s)). The use of grey background can facilitate setting the contrast level. Through experimentation and testing of different grey intensities, a grey color intensity can be identified that matches the green saturation and allowed those images to be less perceptible. Although the example embodiments described herein are discussed with respect to green-based and red-based color, the optical content of the first portion and the second portion may be provided using other color combinations (to match the optical characteristics of the anaglyph glasses worn by the subject).

As discussed herein, the video presentation is intended to, in some embodiments, to help improve the stereoacuity of persons who might be have visual impairment condition such as amblyopia. In such embodiments, the generated video presentation is provided such that the target feature is more prominently visible through the subject's eye affected by amblyopia, with the target feature being less visible on the subject's other eye relative to a level of visibility of the target feature through the subject's eye affected by amblyopia or suppression (which causes deficiency of stereoacuity). The video presentation may be also presented to persons who do not necessarily have a visual impairment problem, for the purpose of improving those persons stereoacuity (e.g., persons who engage in activities requiring good visual acuity and/or good eye-hand coordination). The effect of gain in stereoacuity as measured by the studies and experimentations described herein was limited by the testing methods currently available. Development of better stereoacuity tests, especially for distance stereoacuity, may demonstrate the ability to further optimize stereovision that is considered normal by today's testing standards. Thus, in such situations, the video presentation may be configured so that periodically the color compositions of the identified features are altered such that during one interval of time the target feature is viewable through a first eye (covered by a particular color filtering lens) and the background features are viewable through the other eye, and during a subsequent time interval the target feature is viewable through the other eye (covered by another color filtering lens) while the background features are viewable through the first eye. Thus, the features' color and contrast attributes (determined during generation of the video presentation) are periodically altered, with, for example, the target feature's color being periodically changed from red-based colors to the green-based colors.

In some embodiments, processing of the identified features/objects in the frames/images may be configured to maintain the viewability of the features above a flicker fusion threshold. Thus, in such embodiments, the processing performed on features may include modulating the intensity of at least one of the first portion of the moving images and the second portion of the moving images.

In some example embodiments, the procedure 200 may further include determining the first contrast characteristic of the at least one target feature and the second contrast characteristic of the one or more background features based, at least in part, on contrast testing data for the subject, obtained from a subjective evaluation performed for the subject according to a perceptual contrast testing procedure. The subjective evaluation performed according to the perceptual contrast testing procedure may be performed according to a MARS PERCEPTRIX™ (Mars) exam. In some implementations, determining the first contrast characteristic and the second contrast characteristic may include obtaining the contrast testing data representative of a comparison of Mars exam panels, comprising letters with varying contrast levels, to levels of perception for each eye of the subject, when wearing anaglyph glasses, to the at least one target feature and the at least one background feature, and determining the first contrast characteristic and the second contrast characteristic based on the contrast testing data obtained from the subjective evaluation performed according to the perceptual contrast testing procedure. In such embodiments, determining the first contrast characteristics and the second contrast characteristics may include adjusting the first contrast characteristic and the second contrast characteristic such that a perceived background feature contrast level of the one or more background features, when viewed by a weaker eye covered by one of the lenses of the anaglyph glasses, is reduced for the at least one target feature.

With reference next to FIG. 2B, a flowchart of an example procedure 250 for video presentation to cause controllable stimulation of a subject's eyes is shown. The procedure 250 is generally performed at a video presentation station/unit, for viewing by a subject (who is seeking to improve his/her stereoacuity and vision). The procedure 250 includes obtaining 260 a video presentation comprising successive frames of moving images, with one or more of the successive frames including a selected at least one target feature represented in the moving images and configured to cause stimulation of one of a first eye or a second eye (or both eyes) of the subject, and further including one or more background features, with the at least one target feature being instrumental in carrying out the message or story of the video presentation and being distinguishable from a remainder of the moving images comprising the one or more background features. For at least some of the one or more of the successive frames in which the at least one target feature appears, a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images. As noted, in some embodiments, obtaining the video presentation may include one or more of, for example, receiving a video transmission from a remote device via a communication channel (e.g., a wired or wireless channel), which may occur in real-time (i.e., substantially at the time the video are generated), connecting the remote device to a video presentation unit, or reading video presentation data for the video presentation from a data storage device (e.g., a portable storage device, such as a flash drive or DVD disc). As described herein, in some embodiments, the video presentation is processed at a video processor (e.g., the video processor 110 of FIG. 1) from received source video images (e.g., provided as input from one or more of a remote network server, a non-transitory media such as a DVD or Blu-Ray™ disc played on a DVD/Blu-Ray™ player coupled to the video processor, original source materials prepared by a user, a recording captured via a video camera, etc. The video processor may be configured to identify from the source video images outlines of a first object and one or more second objects, with the first object corresponding to the at least one target feature and the one or more second objects corresponding to the one or more background features. In some example embodiments, the video processor may further be configured to extract the identified outlines of the first object corresponding to the at least one target feature, extract the identified outlines of the one or more second objects, and process the extracted outlines of the first object and the one or more second objects to include optical wavelength characteristics matching a filtering spectrum of anaglyph glasses used by the subject to view the video presentation (e.g., adjusting the color of the outlines of the target feature(s), and possibly the area within the outlines, to a color-set not filtered by one of the filtering lenses of anaglyph glasses worn by the user).

With continued reference to FIG. 2B, the procedure 250 further includes presenting 270 (e.g., using a video presentation unit or station) the prepared video presentation comprising the first portion of the moving images to the first eye of the subject, and the second portion of the moving images to the second eye. In some implementations, presenting the prepared video presentation may include presenting the prepared video presentation to a subject to improve stereoacuity of the subject. Presenting the prepared video presentation may include presenting the prepared video presentation to the subject wearing anaglyph glasses to view the video presentation.

To test and evaluate the efficacy of the implementations described herein to improve stereoacuity and vision in persons, a study was conducted in which children, ages 4-15 years, with amblyopia viewed videos (e.g., 40 minutes daily on an iPad while wearing anaglyph glasses). Eligibility criteria for enrolling subjects included ages 4-18 years, presence of amblyopia defined as best corrected visual acuity (BCVA) of 0.2 log MAR (20/30) or worse at distance, at least 0.2 log MAR (2 lines) interocular difference, ability to fuse Worth 4 Dot (W4D) at near, and no change in vision tested on two consecutive visits at least 4 weeks apart. Strabismus was permitted without restrictions provided that fusion was present on W4D at near. Prior strabismus surgery and intraocular surgery were permitted. Patching 2 hours daily was permitted if children presented while patching and wished to continue to do so during the study. Exclusion criteria included atropine penalization use at the time of enrollment, neurologic disorders that interfered with reliable visual acuity testing, prematurity greater than 8 weeks.

Visual acuity at distance and near, stereoacuity, ocular alignment, suppression, compliance, and subjective experience were assessed at baseline, 2, 4, 8 and 16 weeks. Stereoacuity was tested using Butterfly non-Randot, Randot Stereo, and Randot Preschool Stereoacuity tests with the highest arc seconds measured used for analysis. Power calculations were performed with 80% power to detect a 0.1 log MAR change in BCVA and 0.2 log MAR change in stereoacuity. In order to determine clinically significant change in BCVA, 51 subjects were needed, for stereoacuity 24 subjects were needed.

All subjects underwent baseline testing in the following order.
1) Stereoacuity was assessed with Stereo Butterfly Test (Stereo Optical Co., Inc., Chicago, Ill., USA) which included a Randot butterfly image, 3 non-Randot animals and 9 non-Randot circles.
2) Randot Stereoacuity Test (Stereo Optical Co.,).
3) Randot Preschool Stereoacuity Test (Stereo Optical Co. Inc).
4) Binocular fusion testing was performed using Worth 4 Dot (W4D) testing at distance and near using anaglyph glasses and a handheld W4D flashlight.
5) Strabismus was assessed with alternate cover testing (ACT) using horizontal and vertical prism bars to "overcorrect" and demonstrate a maximum tropia and phoria.
6) Visual acuity (VA) was obtained monocularly at distance with the Electronic Visual Acuity (EVA) system (M&S Technologies, Inc., Niles, Ill., USA) using E-ETDRS or HOTV crowded letters
7) Visual acuity was obtained monocularly at near using a standard near card held at 14 inches from the subject's face.
8) Questionnaires regarding both child and caregiver opinions assessed ease and preference of videos, patching and atropine. Inquiries were also made regarding child's enjoyment of TV watching, frequency of headaches, diplopia and eye straining.

Instructions of 40 minutes daily video watching at home (while parent is in the room to ensure compliance) were given. Intermittent video watching was allowed (10 mins at a time) if desired, provided that 4.5-5.0 hours videos were watched weekly. Testing of stereoacuity, W4D. ACT, distance and near VA, and follow-up questionnaire was repeated at 2, 4, and 8 weeks. Data at a timepoint of 16 weeks was performed by the referring pediatric ophthalmologist (at their office) and obtained by medical record review.

The video presentations for the subjects that participated in the study included 10 episodes (each with a duration of 22-25 minutes) of the cartoon show "Clifford the Big Red Dog-Puppy Days." The generated output videos presented Clifford (the main character) as a red cartoon character against a green and grey background. The contrast level of the fellow eye was set to 20% of the amblyopic eye contrast 100%. All the subjects were asked to "find Clifford" while watching a sample video during enrollment to demonstrate binocular viewing. For sham videos, Clifford was made green and grey, thus eliminating the color and contrast presented to the amblyopic eye and allowing the subject to view the entire video through the fellow eye. Contrast was not increased during video watching but maintained at 15%.

The output video content was prepared using a system with a similar configuration to the system 100 depicted in FIG. 1. The video processor (corresponding to the processor 110 of FIG. 1) was implemented using a computer with an INTEL quad processor, running a Windows 10 operating system. Some of the processing operations (to implement the procedures and processed described herein) were implemented using commercial software applications that included Autodesk NUKE (a digital compositing application). Adobe After effects (a video processing and compositing application), KEYLIGHT (Keying software plugin). Lightwave, Maya, and Adobe suite. Pre-rendered animated content (in this study. "Clifford the big red dog" content) was modified from its original format to isolate the outline of each cartoon characters from the background in the following manner. Pre-rendered or flat animation from HD-DVD source material was obtained, and outlines of characters and background objects were isolated. In addition, colors, other than the red and green wavelengths, were eliminated. The wavelengths of the cartoon characters were then matched to the specific filter spectrum of commercially available Bernell red-green anaglyph glasses (Division of Vision Training Products, Inc., Mishiwaka, Ind.).

While the isolation (extraction) of objects (in full or just their outlines, in which case the interior area within the outlines may be filled with grey color, grey mixed with red and green, or some other color variation) and the subsequent processing of the extracted objects (to control their contrast and color content) can be performed automatically via a processing system implementation such as the one described in relation to FIG. 1, in some situations, some or all of the artistic tasks/operations may be performed by artists. For example, with no matte or isolation layering provided, visual artists may be tasked to separate characters manually through the combination of visualization software and the existing pipeline using a creative process in which existing source content is treated/processed, with the resultant output considered to be proprietary intellectual property in a creative application. For example, a user (artist) may oversee extraction and separation of characters in an input source video using Keylight software inside of NUKE. The Keylight software may be used, for example, with customized processes to identify and isolate color spectrum values.

Isolated/extracted objects (whether in full or just their outlines) may then have their attributes controllably adjusted to, for example, adjust the intensity (gain) of the character and the chromatic values vs the white/grey gamma settings of the background (e.g., 0.55 neutral grey). Some of these attribute control operations may be implemented using the Keylight application.

In the experiments conducted to test the implementations described herein, existing pre-rendered or flat animation from HD-DVD source materials were used. The videos were downloaded from publicly available video achieves on the Internet with permission from Scholastic, Inc. Character and scenery images were extracted from the background (through a combination of visualization software and the existing pipeline). Extraction of each character and scenery images from the background allowed for manipulation of the color hue and saturation of each character, all scenery images, and the underlying background separately. In the experiments, characters were first extracted and separated using, for example, Keylight software inside of NUKE. This allowed the color (hue and saturation) of each character to be modified independently of the background. Custom procedures (implemented using the Keylight application) were then used to specify color hue (wavelength) values. Fine tuning of color wavelengths and background gain (intensity) were occasionally undertaken by adjusting various parameters of the application used.

An example process that may be implemented to adjust the color attributes of features (target and background) presentable to a subject may be the following. A resultant video output can be thought of as comprising multiple separate layers. The first layer may include grey color set to a predetermined level (also referred to as the de-saturation level) that makes the colors in the other layers (superimposed on the grey de-saturation layer) more or less visible. The first layer may correspond to the original input video content that has been desaturated to a grey level, with the other layers corresponding to extracted features from the original input video content (the de-saturated layer may include traces of the at least one target feature and the background features, e.g., appearing in grey-based coloring). Superimposed on the grey de-saturation layer is the target-feature layer in which the identified outline (and/or area inside the outline) is set to red-based colors (a uniform red color may be used, or several red-based colors may be applied to different areas of the at least one target feature). Also superimposed on the grey de-saturation level is the background features layer comprising the features that are to be viewable by the dominant/stronger eye of the subject, with the color of those features set to green-based colors (the features may be set to a uniform green-based color, or several different green-based colors may be used). As discussed herein, the particular colors used for the at least one target feature and the background feature may be based on the color spectrum of the anaglyph glasses, with a first lens, matching the color(s) applied to the at least one target feature, covering the stronger eye so that the at least one target feature become less noticeable when passed through the lens (because it would blend with the similar color of the lens). The second lens, matching the color(s) of the background features, covers the non-dominant/weaker eye, thus making the at least one target feature, presented in color(s) matching the color spectrum of the first lens, more noticeable when passed through the second lens (e.g., the at least one target feature would appear as dark color to the weaker eye covered by the second lens).

Visible colors have both hue and saturation. A color's hue corresponds to a specific wavelength along the visible color spectrum ranging from red to violet. For example, the wavelength of a red hue is typically 635-700 nanometers, while the wavelength of a green hue is typically 520-560 nanometers. The main character in the source video(s) was isolated from the supporting characters and scenery images, and was made red. The wavelength of the main cartoon character was matched to the specific filter spectrum of commercially available Bernell red-green anaglyph glasses (Division of Vision Training Products, Inc., Mishiwaka, Ind.). Matching the optimal wavelength of red that was filtered by the red lens of the anaglyph glasses was determined with subjective testing. This process involved visual comparison of the main character presented in multiple wavelengths ranging across the red spectrum. The red lens was found to filter a red hue with a red-green-blue (RGB) value of 238:13:13.

The supporting cartoon characters and scenery images (e.g., background features) were made green. A green wavelength that was optimally filtered by the green lens of the anaglyph glasses was determined using subjective visual comparison of the supporting characters and scenery images presented in multiple wavelengths ranging across the green spectrum. The green lens was found to filter a green hue with a RGB value of 13:238:124.

A difference in contrast viewed by the right and left eyes defines dichoptic viewing and allows bilateral and simultaneous stimulation of the eyes. Prior studies suggest that successful amblyopia therapy with dichoptic training requires the non-amblyopic eye to view an image with a contrast level that is 10-20% of the contrast level seen by the amblyopic eye at the start of therapy. The background contrast gain was set to optimize specific contrast levels between main and supporting characters/scenery. When the non-amblyopic eye views a less contrasted image, the amblyopic eye is in turn preferentially stimulated.

Contrast of color against a neutral grey background is determined by both its saturation and hue. Saturation of color is defined as the intensity of color, the degree to which color differs from white on a grey scale, or the amount of grey within a color. When the main character, supporting characters and scenery images were converted into red and green hues, the saturation (amount of inherent grey) of each color was optimized to provide a specific level of contrast of each images against the underlying background. However, the contrast of a character/image against a background is not determined solely by saturation (grey intensity) values alone. The color's hue can also influence the perceived contrast of that color. For example, when viewing a yellow line and blue line with equal saturation against a white background, the yellow line will appear to be less contrasted than the blue line. Therefore, in order to determine the amount of contrast presented to the non-amblyopic eye, Mars contrast testing was performed using red-green anaglyph glasses while viewing the red main and green supporting characters/scenery against backgrounds of varying grey intensity.

Standardized contrast testing in the clinic is typically performed with a Mars exam (The Mars Perceptrix Corporation, Chappaqua, N.Y., USA). This clinical tool asks the test-taker to read a series of grey letters on a white background. The letters decrease in intensity (contrast) from black to white, each are assigned contrast values. The level at which the test-taker can no longer identify the letter is recorded as their limit of contrast sensitivity. Mars examination was used to determine a contrast value for the main character, supporting characters and scenery against backgrounds of varying grey intensity. A total of 16 non-amblyopic and 2 amblyopic adults were asked to subjectively equate a grey letter on a Mars testing panel with the contrast level of the main and supporting characters against backgrounds of varying grey intensity. All were examined while wearing red-green anaglyph glasses with a 0.3 Bangarter filter over the red lens. Subjects were asked to provide 4 grey letter values that matched the contrast of the following images: (1) the red main character viewed through the red lens (2) the red main character viewed through the green lens (3) the green character viewed through the red lens (4) the green character viewed through the green lens. When the background was set at white, all characters were highly contrasted. When the background was changed to a medium grey intensity with a specific gamma setting of 0.55 neutral grey with RBG values set to 237:242:240, the average contrast scores of the red main character were found to be the highest when viewed through the green lens and lowest when viewed through the red lens. Analysis of Mars contrast values with the specific RBG values stated for above, showed that the red main character was seen with 6.35 times greater contrast when viewed through the green lens than when viewed through the red lens. This meant that the red main character viewed through the red lens was seen with $1/6.35=15.7\%$ of the contrast compared with the main character when viewed through the green lens. This level of contrast differentiation between the eyes provided the 80-90% contrast difference shown in previous studies to be effective for dichoptic amblyopia therapy. In prior studies, the contrast difference was adjusted from 90% (large difference between the eyes) to 10% (small difference between the eyes) during the course of treatment and subjects whose amblyopia improved, further improved when contrast difference was decreased. It may be possible that a larger range of contrast difference, for example 5-90% may ultimately be effective for subjects with specific levels of visual acuity and stereoacuity defects.

By working with these now independent layers at these set values in Adobe After effects, a color was created that treated final composited image that included a red main character, green supporting characters and scenery images, and grey background.

Testing to determine the ability of the program to anti-suppress the amblyopic eye was performed with two adults with moderate amblyopia, one with manifest strabismus and one without strabismus. Both were known to suppress their amblyopic eye at distance and fuse at near on Worth-4-dot testing. The program was unable to fully anti-suppress the amblyopic eye of the strabismic adult, but was able to consistently anti-suppress the non-strabismic adult. Bangarter filters of increasing strength were then introduced over the red lens to determine at what level anti-suppression occurred. A 0.3 log MAR Bangarter filter was found to consistently anti-suppress both subjects for duration of at least 10 minutes of viewing time.

Results of the study described above showed that after 4 weeks, mean improvement in stereoacuity of 0.362 log MAR (CI 0.167-0.557; p=0.0009) was seen in 63% of children (CI 41%-82%). Mean distance VA improved 0.043 log MAR (CI 0.007-0.08; p=0.022). Worth-4-dot testing showed recovery of central fusion in 56% of children. Compliance with 80% of prescribed viewing time was 77%. No adverse effects were reported.

Figure 3:
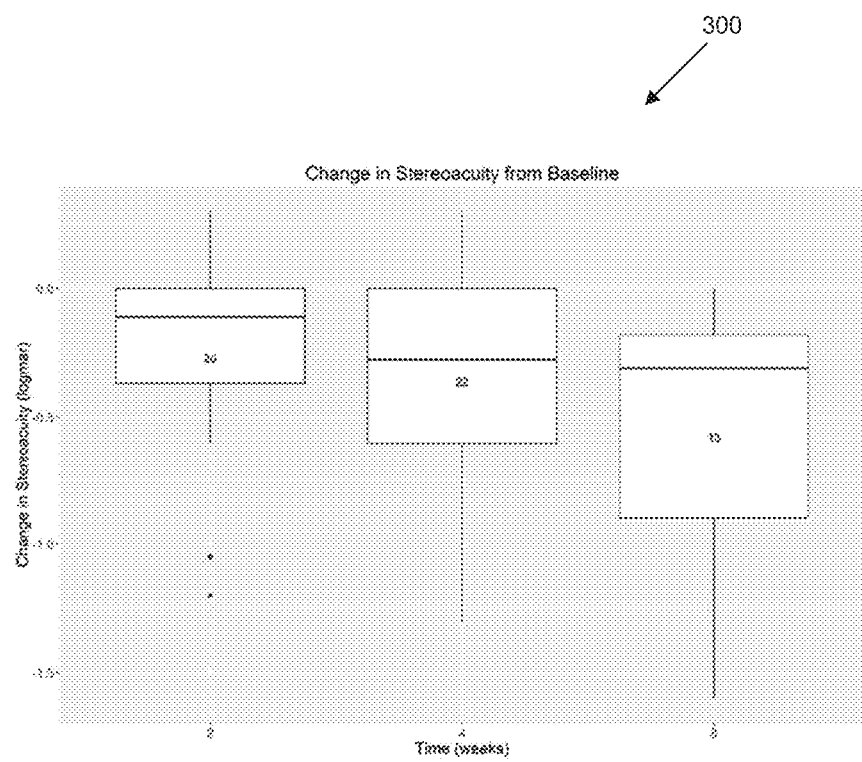
FIG. 3 is a graph showing improved results in stereoacuity over a period of time.

FIG. 3 includes a graph 300 showing improvement in stereoacuity over a period of time during which subjects viewed the generated videos (including target and background features whose attributes were controllably adjusted in a manner similar to that described herein). Boxplot of stereoacuity scores in log MAR show that the primary endpoint was 4 weeks, at which time stereoacuity was clinically and statistically improved. The maximum effect was seen at the 8-week timepoint, after which time only 2 subjects continued viewing videos to the 16-week timepoint. Despite discontinuation of videos at 8 weeks, the effect of improved stereoacuity is persistent and remains both clinically and statistically significant.

Figure 4:
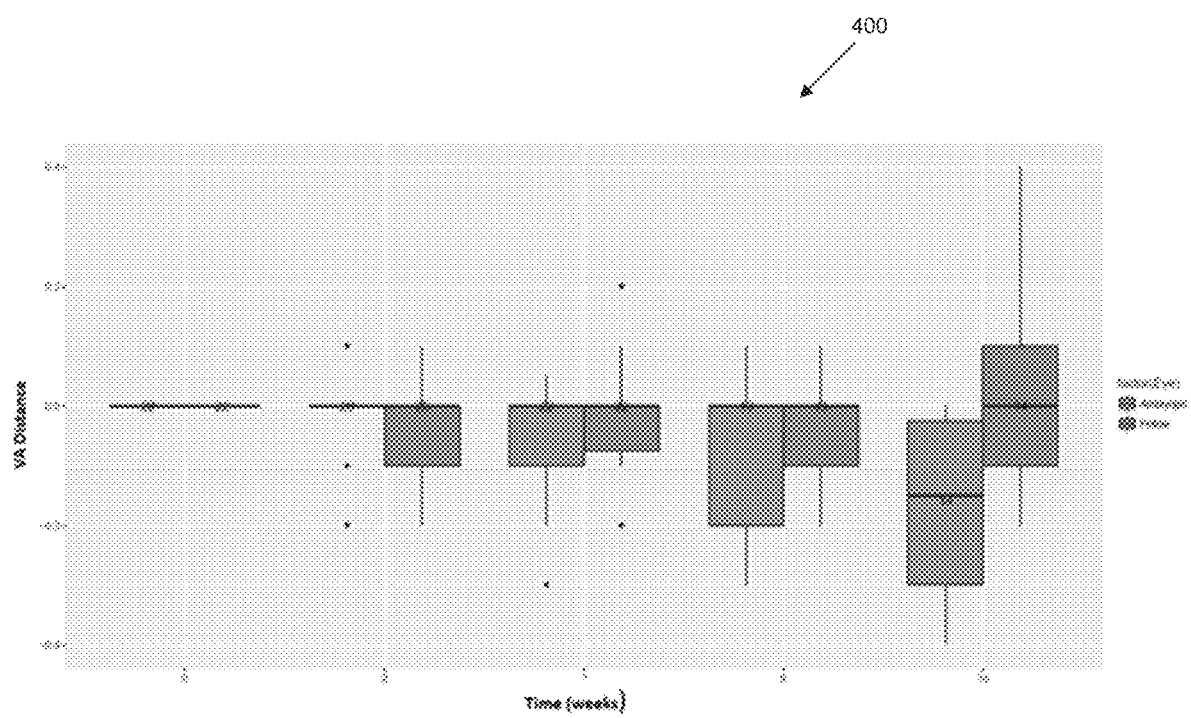
FIG. 4 is a graph showing improved results in distance visual acuity (VA) over time.

FIG. 4 includes a graph 400 showing improvement in distance visual acuity (VA) over time. Of the 22 subjects tested, 7 (32%) showed improvement in vision that was clinically significant (gain of at least 0.1 log MAR). The results illustrated in the graph show that the distance VA steadily improved over 16 weeks despite discontinuation of video viewing at 4 weeks. Boxplot of change in distance VA scores shows improved acuity in the amblyopic eye at 16 weeks even though 90% of children ($12/14$) stopped watching the videos at 4 weeks. Patching and/or atropine was started at the 8-week time point in subjects that previously failed this standard of care therapy. After watching the video program for 4-8 weeks and restarting standard therapy, additional vision was gained. This suggests that the video program may "jump start" or "release the brakes" on visual system that previously halted development. Viewing of this program may allow the brain to achieve further gains in vision than can currently be achieved with standard therapy alone.

Figure 5:
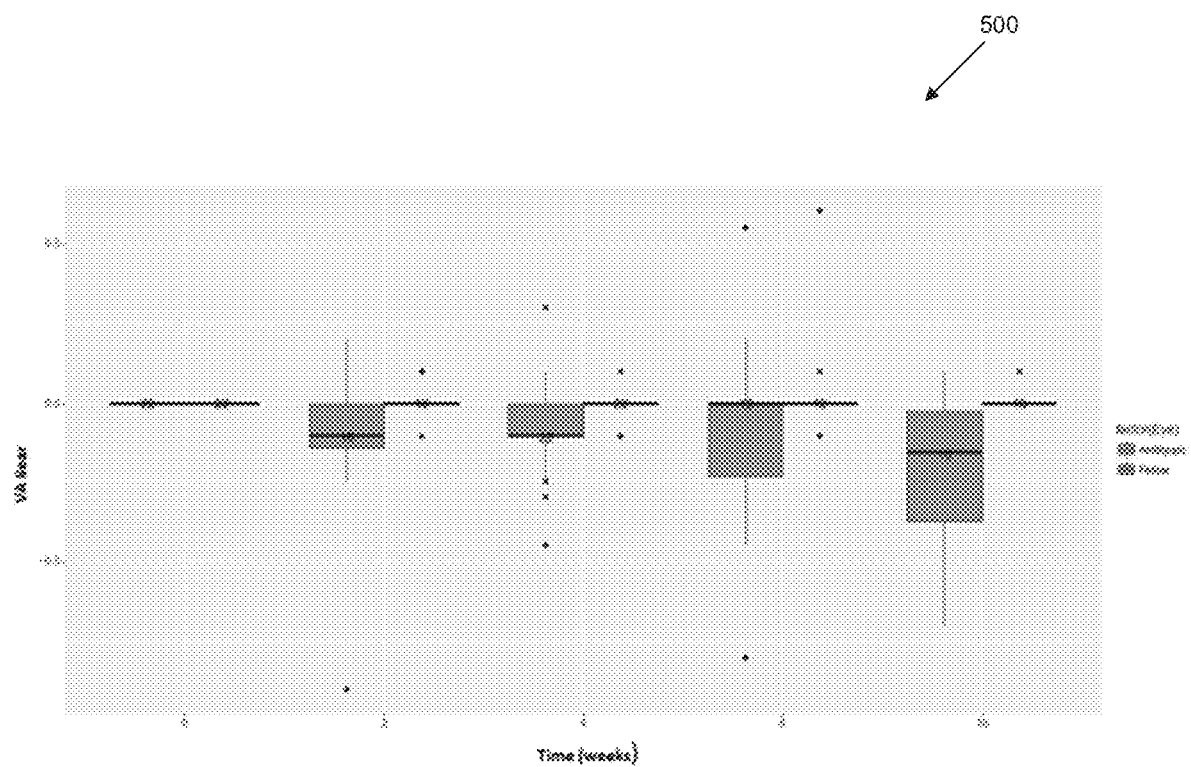
FIG. 5 is a graph showing improved results in near visual acuity (VA) over time.

FIG. 5 includes a graph 500 showing improvement in near visual acuity (VA) over time. Of the 22 subjects tested, 12 (55%) showed improvement in vision that was clinically significant (gain of at least 0.1 log MAR). The results illustrated in the graph show that the near VA steadily improves over 16 weeks despite discontinuation of video viewing at 4 weeks. Boxplot of near VA scores shows improved mean acuity in the amblyopic eye at 16 weeks even though 90% of children ($12/14$) stopped watching the videos at 4 weeks. Patching and/or atropine was started at the 8-week time point in subjects that previously failed this standard of care therapy. After watching the video program for 4-8 weeks and restarting standard therapy, additional vision was gained. The interocular difference in near VA is greatest at 16 weeks which reflects plasticity of the visual system even in previously treated subjects.

Figure 6:
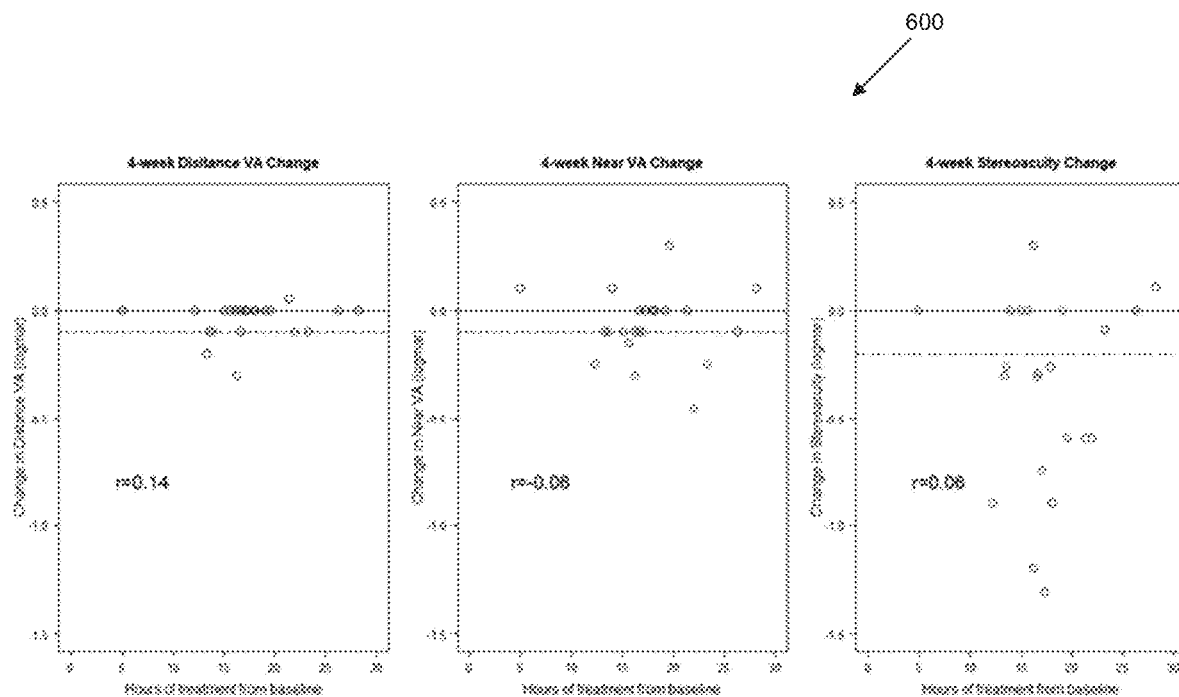
FIG. 6 is a scatterplot showing improved distance VA, near VA and stereoacuity plotted against hours of videos watched.

FIG. 6 includes a scatterplot diagram 600 showing that the hours of viewing did not correlate with change in visual acuity at distance or near, or with stereoacuity. Of the 22 subjects tested, 14 (64%) showed improve stereoacuity that was clinically significant (gain of at least 0.2 log MAR). There was no statistical correlation of acuity improvement with treatment hours, and no threshold minimal number of hours was identified by correlation analysis. Improved stereoacuity and distance acuity did not reach statistical significant until the 4-week primary endpoint.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims. "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A method for video presentation to cause controllable stimulation of a subject's eyes, the method comprising:
    preparing a video presentation including successive frames of moving images;
    wherein for one or more of the successive frames:
        selecting at least one target feature represented in the moving images, with the moving images further comprising one or more background features, the at least one target feature causing stimulation of one of a first eye or a second eye of the subject, with the at least one target feature being instrumental in carrying out the message or story of the video presentation and being distinguishable from a remainder of the moving images comprising the one or more background features, wherein for at least some of the one or more of the successive frames in which the at least one target feature appears:
            controlling a first contrast characteristic of the at least one target feature in each frame of the moving images in which the at least one target feature is present to form a first portion of the moving images; and
            controlling a second contrast characteristic of the one or more background features in the each frame of the moving images in which the one or more background features are present to form a second portion of the moving images; and
        providing the prepared video presentation comprising the first portion of the moving images configured to be presented to the first eye of the subject, and the second portion of the moving images configured to be presented to the second eye of the subject.

2. The method of claim 1, wherein providing the prepared video presentation comprises:
    storing the prepared video presentation on a data storage device configured to be read at a subsequent time instance by a video player device for presentation of the stored video presentation to the subject.

3. The method of claim 1, wherein providing the prepared video presentation comprises:
    presenting the first portion of the moving images and the second portion of the moving images to the first eye and the second eye of the subject improves stereoacuity of the subject.

4. The method of claim 1, wherein providing the first portion and the second portion of the moving images comprises:
    generating a dichoptic video presentation comprising the first portion of the moving images and the second portion of the moving images, including:
        presenting the first portion of the moving images in first one or more colors that are visible through a first filtering lens configured to inhibit visibility of second one or more colors; and
        presenting the second portion of the moving images in the second one or more colors that are visible through a second filtering lens configured to inhibit visibility of the first one or more colors.

5. The method of claim 4, wherein presenting the first portion of the moving images in the first one or more colors comprises presenting the first portion of the moving images in a red-based color visible through a green-based filtering lens and suppressed by a red-based filtering lens, and wherein presenting the second portion of the moving images in the second one or more colors comprises presenting the second portion of the moving images in a green-based color visible through the red-based filtering lens and suppressed by the green-based filtering lens.

6. The method of claim 5, wherein presenting the second portion of the moving images in the green-based color comprises:
    presenting the second portion of the moving images in a green-and-grey color combination visible through the red-based filtering lens and suppressed by the green-based filtering lens.

7. The method of claim 4, wherein presenting the first portion of the moving images in the first one or more colors comprises presenting the first portion of the moving images in a green-based color visible through a red-based filtering lens and suppressed by a green-based filtering lens, and wherein presenting the second portion of the moving images in the second one or more colors comprises presenting the second portion of the moving images in a red-based color visible through the green-based filtering lens and suppressed by the red-based filtering lens.

8. The method of claim 1, wherein providing the prepared video presentation further comprises:
    presenting the first portion of the moving images to the first eye affected by an amblyopia condition.

9. The method of claim 1, wherein preparing the video presentation comprises:
    generating an animated video presentation comprising an animated target feature and animated one or more background features.

10. The method of claim 1, wherein preparing the video presentation comprises:
    receiving source video images; and
    identifying from the source video images outlines of a first object and one or more second objects, wherein the first object corresponds to the at least one target feature and the one or more second objects correspond to the one or more background features.

11. The method of claim 10, further comprising:
extracting the identified outlines of the first object corresponding to the at least one target feature;
extracting the identified outlines of the one or more second objects; and
processing the extracted outlines of the first object and the one or more second objects to include optical wavelength characteristics matching a filtering spectrum of anaglyph glasses used by the subject to view the video presentation.

12. The method of claim 11, wherein processing the extracted outlines comprises:
controllably adjusting gain values for the extracted outlines of the first object and the one or more second objects;
controllably adjusting luminance of the moving images; and
controllably adjusting chromatic components for the first object and the one or more second objects.

13. The method of claim 1, wherein controlling the second contrast characteristic of the one or more background features comprises:
applying the second contrast characteristic to the one or more background features so that, when viewed by the subject, a perceived background feature contrast level of the one or more background features is approximately 10-20% of a perceived target feature contrast level for the at least one target feature.

14. The method of claim 1, further comprising:
determining the first contrast characteristic of the at least one target feature and the second contrast characteristic of the one or more background features based, at least in part, on contrast testing data for the subject, obtained from a subjective evaluation performed for the subject according to a perceptual contrast testing procedure.

15. The method of claim 14, wherein the subjective evaluation performed according to the perceptual contrast testing procedure is performed according to a MARS PERCEPTRIX™ (Mars) exam.

16. The method of claim 15, wherein determining the first contrast characteristic and the second contrast characteristic comprises:
obtaining the contrast testing data representative of a comparison of Mars exam panels, comprising letters with varying contrast levels, to levels of perception for each eye of the subject, when wearing anaglyph glasses, to the at least one target feature and the at least one background feature; and
determining the first contrast characteristic and the second contrast characteristic based on the contrast testing data obtained from the subjective evaluation performed according to a perceptual contrast testing procedure.

17. The method of claim 16 wherein determining the first contrast characteristics and the second contrast characteristics comprises:
adjusting the first contrast characteristic and the second contrast characteristic such that a perceived background feature contrast level of the one or more background features, when viewed by a weaker eye covered by one of the lenses of the anaglyph glasses, is reduced for the at least one target feature.

18. The method of claim 1 wherein the second contrast characteristic has a lower contrast than the first contrast characteristic.

19. The method of claim 1 further comprising modulating the intensity of at least one of the first portion of the moving images and second portion of the moving images.

20. The method of claim 1, further comprising presenting the video presentation to a subject affected by deficient stereoacuity or amblyopia.

21. The method of claim 1 further comprising presenting the video presentation to achieve stereoacuity improvements in vision characteristics of a subject with normal stereoacuity levels.

22. The method of claim 21, wherein presenting the video presentation to the subject affected by the amblyopia condition comprises:
presenting the video presentation to the subject such that the at least one target feature is more prominently visible through the subject's eye affected by the amblyopia condition, with the at least one target feature being less visible on the subject's other eye relative to a level of visibility of the at least one target feature through the subject's eye affected by the amblyopia condition.

23. A system for video presentation to cause controllable stimulation of a subject's eyes, the system comprising:
a video processor configured to:
prepare a video presentation including successive frames of moving images;
wherein for one or more of the successive frames, the video processor is configured to:
select at least one target feature represented in the moving images, with the moving images further comprising one or more background features, the at least one target feature causing stimulation of one of a first eye or a second eye of the subject, with the at least one target feature being instrumental in carrying out the message or story of the video presentation and being distinguishable from a remainder of the moving images comprising the one or more background features;
for at least some of the one or more of the successive frames in which the at least one target feature appears, the video processor is configured to:
control a first contrast characteristic of the at least one target feature in each frame of the moving images in which the at least one target feature is present to form a first portion of the moving images; and
control a second contrast characteristic of the one or more background features in the each frame of the moving images in which the one or more background features are present to form a second portion of the moving images; and
an output device configured to provide the prepared video presentation comprising the first portion of the moving images configured to be presented to the first eye of the subject, and the second portion of the moving images configured to be presented to the second eye of the subject.

24. The system of claim 23, wherein the output device comprises:
a storage device to store output video data representative of the prepared video presentation, the output video data configured to be read at a subsequent time instance by a video player device for presentation of the stored video presentation to the subject.

25. The system of claim 23, wherein the output device comprises:
a video presentation unit configured to present the first portion of the moving images and the second portion of the moving images to the first eye and the second eye of the subject such that the first portion of the images is presented to the first eye and the second portion of the images is presented to the second eye of the subject.

26. The system of claim 25, further comprising:
anaglyph glasses wearable by the subject to view the video presentation.

27. A kit comprising:
a video storage device comprising non-transitory video-recording medium storing video data representative of successive frames of moving images;
wherein one or more of the successive frames include a selected at least one target feature represented in the moving images, with the moving images further comprising one or more background features, the at least one target feature causing stimulation of one of a first eye or a second eye of the subject, with the at least one target feature being instrumental in carrying out the message or story of the video presentation and being distinguishable from a remainder of the moving images comprising the one or more background features,
and wherein for at least some of the one or more of the successive frames in which the at least one target feature appears a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images; and
anaglyph glasses wearable by a subject to view a video presentation generated when the video data representative of the successive frames of the moving images is decoded and played on a video presentation unit.

28. The kit of claim 27, further comprising:
the video presentation unit.

29. A method for video presentation to cause controllable stimulation of a subject's eyes, the method comprising:
obtaining a video presentation comprising successive frames of moving images, wherein one or more of the successive frames include a selected at least one target feature represented in the moving images and configured to cause stimulation of one of a first eye or a second eye of the subject, and one or more background features, with the at least one target feature being instrumental in carrying out the message or story of the video presentation and being distinguishable from a remainder of the moving images comprising the one or more background features, wherein for at least some of the one or more of the successive frames in which the at least one target feature appears a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images; and
presenting the prepared video presentation comprising the first portion of the moving images to the first eye of the subject, and the second portion of the moving images to the second eye of the subject.

30. The method of claim 29, wherein obtaining the video presentation comprises one or more of:
receiving a video transmission from a remote device via a communication channel connecting the remote device to a video presentation unit, or
reading video presentation data for the video presentation from a data storage device.

31. The method of claim 29, wherein presenting the prepared video presentation comprises:
presenting the prepared video presentation to a subject to improve stereoacuity of the subject.

32. The method of claim 29, wherein the video presentation is processed at a video processor from received source video images, the video processor configured to:
identify from the source video images outlines of a first object and one or more second objects, wherein the first object corresponds to the at least one target feature and the one or more second objects correspond to the one or more background features.

33. The method of claim 32, wherein the video processor is further configured to:
extract the identified outlines of the first object corresponding to the at least one target feature;
extract the identified outlines of the one or more second objects; and
process the extracted outlines of the first object and the one or more second objects to include optical wavelength characteristics matching a filtering spectrum of anaglyph glasses used by the subject to view the video presentation.

34. The method of claim 29, wherein presenting the prepared video presentation comprises:
presenting the prepared video presentation to the subject wearing anaglyph glasses to view the video presentation.

35. A video storage device comprising:
non-transitory video-recording medium storing video data representative of successive frames of moving images;
wherein one or more of the successive frames include a selected at least one target feature represented in the moving images, with the moving images further comprising one or more background features, the at least one target feature causing stimulation of one of a first eye or a second eye of the subject, with the at least one target feature being instrumental in carrying out the message or story of the video presentation and being distinguishable from a remainder of the moving images comprising the one or more background features,
and wherein for at least some of the one or more of the successive frames in which the at least one target feature appears a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images.

36. A kit comprising:
a video access device to access video data representative of successive frames of moving images;
wherein one or more of the successive frames include a selected at least one target feature represented in the moving images, with the moving images further comprising one or more background features, the at least one target feature causing stimulation of one of a first eye or a second eye of the subject, with the at least one target feature being instrumental in carrying out the message or story of the video presentation and being distinguishable from a remainder of the moving images comprising the one or more background features, and wherein for at least some of the one or more of the successive frames in which the at least one target feature appears a first contrast characteristic of the at least one target feature in each frame of the moving images in which the at least one target feature is present is controllably adjusted to form a first portion of the moving images, and a second contrast characteristic of the one or more background features in the each frame of the moving images in which the one or more background features are present is controllably adjusted to form a second portion of the moving images; and anaglyph glasses wearable by a subject to view a video presentation generated when the video data representative of the successive frames of the moving images is decoded and played on a video presentation unit.

37. The kit of claim 36, wherein the video access device is configured to access one or more of:

a video storage device comprising non-transitory video-recording medium storing the video data; or a remote device configured to stream the video data to a device accessible by the subject.

* * * * *